United States Patent [19]

Wells et al.

[11] Patent Number: 5,853,707
[45] Date of Patent: Dec. 29, 1998

[54] CONDITIONING SHAMPOOS CONTAINING POLYVALENT METAL CATIONS

[75] Inventors: Robert Lee Wells, Cincinnati; Michael Albert Snyder, Mason; Lisa Ann Napolione, Cincinnati, all of Ohio

[73] Assignee: The Procter & Gamble Co., Cincinnati, Ohio

[21] Appl. No.: 493,400

[22] Filed: Jun. 22, 1995

Related U.S. Application Data

[63] Continuation of Ser. No. 85,695, Jun. 30, 1993, abandoned.

[51] Int. Cl.$^6$ ............................... H61K 7/00; H61K 7/07
[52] U.S. Cl. ...................... 424/70.12; 424/70.11; 424/70.1
[58] Field of Search ...................... 424/70.1, 70.11, 424/70.12

[56] References Cited

U.S. PATENT DOCUMENTS 3,842,847 10/1974 Hewitt ................................ 132/7
4,614,200 9/1986 Hsiung ................................ 132/7
5,120,532 6/1992 Wells ................................ 424/70

*Primary Examiner*—Sally Gardner-Lane
*Attorney, Agent, or Firm*—David K. Dabbiere; Leonard W. Lewis; William J. Winter

[57] ABSTRACT

Provides hair conditioning shampoo compositions suitable and safe for frequent (e.g., daily) use and contact with the hair and skin, said compositions comprising: (a) one or more detersive surfactants such as those selected from the group consisting of anionic, nonionic, amphoteric, and zwitterionic surfactants;(b) a nonvolatile hair conditioning agent or combination of nonvolatile hair conditioning agents selected from the group consisting of insoluble silicones, water soluble organic cationic conditioning agents such as cationic surfactants and cationic polymers; and (c) from about 20% to about 99.5%, by weight, water; wherein said composition additionally comprises from about 0.004M to about 0.08M of free polyvalent metal cations. The present invention can provide improved consistency of deposition on the hair for nonvolatile, insoluble silicone and water soluble cationic conditioning agents when the composition is applied using water across a broad range of hardness.

15 Claims, No Drawings

CONDITIONING SHAMPOOS CONTAINING POLYVALENT METAL CATIONS

This is a continuation of application Ser. No. 08/085,695, filed on Jun. 30, 1993, now abandoned.

FIELD OF THE INVENTION

This invention relates to shampoo compositions containing hair conditioning ingredients. More particularly, this invention relates to shampoos containing hair conditioning agents such as insoluble silicones, cationic surfactants, cationic polymers, or mixtures thereof, and additionally containing polyvalent metal cations.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing cleans the hair by removing excess soil and sebum. However, the shampooing process has disadvantages in that the hair can be left in a wet, tangled, and generally unmanageable state. Shampooing can also result in a dry or "frizzy" condition of the hair, and a loss of luster, due to removal of natural oils and other hair moisturizing materials. After shampooing, the hair can also suffer from a loss of "softness" as perceived by the user, upon drying. The hair can further suffer from increased levels of static upon drying after shampooing. This can interfere with combing and can result in a state whereby the hair becomes excessively fluffy and difficult to retain in an aligned condition. This is sometimes referred to as fly-away hair.

A variety of approaches have been developed to alleviate after-shampoo problems of the hair. These range from post-shampoo application of hair conditioners, e.g., hair rinses to the inclusion of hair conditioning aids in shampoos. Hair rinses are applied in a separate step following the shampooing, left on the hair for a length of time, and then rinsed with fresh water. Other post-shampoo conditioning aids, such as hair tonics, hair gels, and hair lotions, are also applied to the hair as a separate step. This, of course, is time consuming and is not as convenient as shampooing and conditioning the hair in a single step. Shampoos which both clean and condition the hair are highly desirable products, and are favored by a substantial population of consumers in the marketplace.

In order to provide hair conditioning benefits in shampoos, a wide variety of conditioning actives have been proposed. These include: oils and oil-like materials, such as hydrocarbon liquids, fatty alcohols, monocarboxylic acid esters, and polyhydric alcohol esters; silicones such as soluble silicones, e.g. dimethicone copolyols, and insoluble silicones, such as polydimethylsiloxane; and cationic conditioning agents, including water insoluble cationic surfactants (primarily for static control) and water soluble cationic surfactants and cationic polymers (for static control as well as wet detangling and wet hair feel).

It is especially preferred to include insoluble silicones, for the excellent dry hair feel and combing benefits they can provide, and water soluble cationic surfactants and/or polymers, for the excellent wet hair detangling and wet hair feel they can provide.

It is well known in the hair conditioning art that different types of hair require different types and amounts of conditioning in order for the user to experience optimal conditioning. It has been found, in particular, for instance, that dry, damaged, color treated, and permed hairs typically have the greatest need for the conditioning benefits of insoluble silicones and water soluble cationic conditioning agents.

It hardly needs to be said that in designing conditioning shampoos for particular types of hair, it is critical for widespread success in the marketplace that persons with the targeted hair type obtain the benefits intended for the conditioning product. It is important that they obtain the needed conditioning performance regardless of where they may live or use the product.

However, it has now been found that conditioning shampoos containing insoluble silicones and/or water soluble cationic conditioning agents can have widely differing performance on the same hair types depending upon where the person using the product is located. In particular, it has been found that hardness of the water used to wash and rinse the hair can affect both insoluble silicone and cationic conditioning agent performance. For example, hard water increases the deposition on hair of soluble cationic conditioning agents such as water soluble cationic polymers, but decreases the deposition on hair of nonvolatile silicone. Conversely, soft water decreases the deposition on hair of soluble cationic conditioning agents, and increases the deposition on hair of insoluble silicone.

A practical example of the net result of this is that a hair conditioning shampoo designed for providing optimum conditioning of hair in soft water, utilizing nonionic insoluble silicone and cationic surfactant and/or polymer, will perform as expected in soft water, but in hard water will tend to result in poor dry hair feel and poor dry combing, due to low silicone deposition, and a slick, oily feel, due to too much cationic conditioner deposition. Conversely, a conditioning shampoo designed for providing optimum conditioning of hair in hard water will perform as intended in hard water. However in soft water, the same product will tend to result in hair having a heavy, coated feel, due to too much silicone deposition (particularly upon frequent usage), and poor wet hair feel and poor wet detangling, due to too little cationic conditioner deposition.

It is an object of this invention to provide conditioning shampoo compositions containing insoluble silicones that provide improved consistency of conditioning performance for the hair regardless of whether the composition is used in hard or soft water.

It is also an object of this invention to provide conditioning shampoo compositions containing water soluble cationic surfactants, cationic polymers or mixtures thereof, as cationic hair conditioning agents, that provide improved consistency of conditioning performance for the hair regardless of whether the composition is used in hard or soft water.

It is another object of this invention to provide conditioning shampoo compositions containing a mixture of insoluble silicone and cationic conditioning agent, such as cationic surfactants, cationic polymers, or a mixture thereof, that provide improved consistency of conditioning performance to the hair regardless of whether the composition is used in hard or soft water.

It is yet another object of the invention to provide a method for making conditioning shampoo compositions which meet the above objects.

These and other benefits as may be apparent to those skilled in the art or otherwise described herein can be obtained according to the present invention, which is described below.

Unless otherwise indicated, all percentages and ratios are by weight. Unless otherwise indicated, all weight percentages are calculated based upon the total weight of the composition.

The invention hereof can comprise, consist of, or consist essentially of the essential elements and limitations of the invention described herein, as well any of the additional ingredients, components, or limitations described herein.

As used herein, the terms "soluble" and "insoluble" used in reference to particular ingredients of the shampoo compositions refer to solubility or insolubility, respectively, of that ingredient in the shampoo composition, unless otherwise specifically indicated. For example, the terms "water soluble" and "water insoluble", as used herein, specifically refer to solubility in water as being required as opposed to requiring solubility or insolubility in the composition. Such ingredient may also be soluble or insoluble in the composition, but it need not necessarily be for purposes of the invention.

All documents referred to herein, including all patents, patent applications, and printed publications, are hereby incorporated by reference in their entirety into this disclosure.

SUMMARY OF THE INVENTION

The present invention provides hair conditioning shampoo compositions suitable and safe for frequent (e.g., daily) use and contact with the hair and skin, said compositions comprising:

(a) one or more detersive surfactants such as those selected from the group consisting of anionic, nonionic, amphoteric, and zwitterionic surfactants;

(b) a nonvolatile hair conditioning agent or combination of nonvolatile hair conditioning agents selected from the group consisting of insoluble silicones, water soluble organic cationic conditioning agents such as cationic surfactants and cationic polymers; and (c) from about 20% to about 99.5%, by weight, water; wherein said composition additionally comprises from about 0.004M to about 0.08M of free polyvalent metal cations.

The present invention can provide improved consistency of deposition on the hair for nonvolatile, insoluble silicone and water soluble cationic conditioning agents when the composition is applied using water across a broad range of hardness. By increasing the hardness level of the water in the compositions hereof, it has been found that more consistent deposition can be obtained regardless of the hardness of the water being used to wet and rinse the hair. This, in turn, provides the product formulator with the ability to design formulations for particular hair types which will perform as intended without regard to the whether the product is being used in a hard or soft water area. It can provide the user with conditioning performance more closely aligned with what the product formulation intended and with what the expectations of the user are, based on the largest target hair type regardless of whether the user lives in a hard or soft water area. It also provides the user with more consistent conditioning results regardless of whether he or she is traveling from hard water to soft water areas, or vice versa.

The present invention further provides a process for making conditioning shampoo compositions as described above.

DETAILED DESCRIPTION OF THE INVENTION

Detersive Surfactant Component

The compositions of the present invention contain a detersive surfactant component, which can comprise one or more anionic, nonionic, amphoteric, or zwitterionic surfactants. The purpose of the detersive surfactant is to provide cleaning performance to the composition. The compositions hereof will preferably comprise at least one anionic surfactant.

The detersive surfactant component will generally be present at a level from about 5% to about 50%, preferably from about 8% to about 30%, more preferably from about 10% to about 25%, of the composition.

Anionic Surfactants

Anionic surfactants are preferred to be included in the compositions hereof. Typically, they will be present at a level of from about 5% to about 30%, preferably from about 7% to about 25%, more preferably from about 8% to about 20%, most preferably from about 9% to about 18%, by weight of the composition. Anionic detersive detergents useful herein include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to 10, and M is a cation such as $H^+$, ammonium, alkanolamines, such as triethanolamine, monovalent metals, such as sodium and potassium, and polyvalent metal cations, such as magnesium, and calcium. The cation M, of the anionic surfactant should be chosen such that the anionic surfactant component is water soluble. Solubility will depend upon the particular anionic surfactants and cations chosen. If polyvalent cations are used as the counterions for anionic surfactant, it should be recognized that the level of such surfactant must be limited so that the level of polyvalent metal cations present as free ions in the shampoo does not exceed the maximum level of the present invention. It will be preferably, if soluble salts of polyvalent metal anionic surfactants are used, to utilize them in combination with monovalent metal salts of anionic surfactants, or with amphoteric, nonionic, or zwitterionic surfactants, or combinations thereof.

Those skilled in the art will recognize that many polyvalent metal salts of anionic surfactants are less water soluble than their monovalent counterparts. As an aid to determining appropriate mixtures of anionic surfactants, the anionic surfactants should be chosen such that the Krafft temperature of the surfactants chosen is about 15° C. or less, preferably about 10° C. or less, more preferably about 0° or less. It is also preferred that the anionic surfactant be soluble in the composition hereof.

Krafft temperature refers to the point at which solubility of an ionic surfactant becomes determined by crystal lattice energy and heat of hydration, and corresponds to a point at which solubility undergoes a sharp, discontinuous increase with increasing temperature. Each type of surfactant will have its own characteristic Krafft temperature. Krafft temperature for ionic surfactants is, in general, well known and understood in the art. See, for example, Myers, Drew, *Surfactant Science and Technology*, p.p. 82–85, VCH Publishers, Inc. (New York, N.Y., USA), 1988 (ISBN 0-89573-399-0).

Preferably, R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic detersive surfactants are the water-soluble salts of the organic, sulfuric acid reaction products of the general formula:

wherein $R_1$ is chosen from the group consisting of a straight or branched chain, saturated aliphatic hydrocarbon radical having from about 8 to about 24, preferably about 12 to about 18, carbon atoms; and M is a cation, as previously described, subject to the same limitations regarding polyvalent metal cations as previously discussed. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{12-18}$ n-paraffins.

Additional examples of synthetic anionic detersive surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other synthetic anionic detersive surfactants of this variety are set forth in U.S. Pat. Nos. 2,486,921; 2,486,922; and 2,396,278.

Still other synthetic anionic detersive surfactants are in the class designated as succinnates. This class includes such surface active agents as disodium N-octadecylsulfosuccinnate; tetrasodium N-(1,2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid.

Other suitable anionic detersive surfactants include olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, Pflaumer and Kessler, issued Jul. 25, 1967, incorporated herein by reference.

Another class of anionic detersive surfactants are the bata-alkyl-oxy alkane sulfonates. These compounds have the following formula:

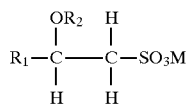

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Many additional synthetic anionic surfactants are described in *McCutcheon's, Emulsifiers and Detergents,* 1989 *Annual,* published by M. C. Publishing Co., which is incorporated herein by reference. Also U.S. Pat. No. 3,929, 678, Laughlin et al., issued Dec. 30, 1975, discloses many other anionic as well as other surfactant types and is incorporated herein by reference.

Preferred anionic detersive surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric and Zwitterionic Surfactants

Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Zwitterionic detersive surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

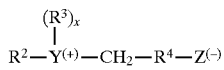

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines and amidosultaines can advantageously be utilized as foam enhancing surfactants that are mild to the eye in partial replacement of anionic surfactants. Sultaines, including amidosultaines, include for example, cocodimethylpropylsultaine, stearyidimethylpropylsultaine, lauryl-bis-(2-hydroxyethyl) propylsultaine and the like; and the amidosultaines such as cocoamidodimethylpropylsultaine, stearylamidododimethylpropylsultaine, laurylamidobis-(2-hydroxyethyl) propylsultaine, and the like. Preferred are amidohydroxysultaines such as the $C_{12}$–$C_{18}$ hydrocarbyl amidopropyl hydroxysultaines, especially $C_{12}$–$C_{14}$ hydrocarbyl amido propyl hydroxysultaines, e.g., laurylamidopropyl hydroxysultaine and cocamidopropyl hydroxysultaine. Other sultaines are disclosed in U.S. Pat. No. 3,950,417, issued Apr. 13, 1976, incorporated herein by reference.

Another specific class of amphoteric surfactants is defined by the aminoalkanoates of the formula:

and the iminodialkanoates of the formula:

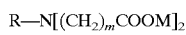

and mixtures thereof; wherein n and m are numbers from 1 to 4, R is $C_8$–$C_{22}$ alkyl or alkenyl, and M is hydrogen, alkali metal, alkaline earth metal, ammonium or alkanolammonium.

Examples of amphoteric surfactants falling within the aminoalkanoate formula include n-alkylamino-propionates and n-alkyliminodipropionates. Such materials are sold under the tradename DERIPHAT by Henkel and MIRATAINE by Miranol, Inc. Specific examples include N-lauryl-beta-amino propionic acid or salts thereof, and N-lauryl-beta-imino-dipropionic acid (DERIPHAT 160C) or salts thereof, and mixtures thereof.

Other amphoteric surfactants are depicted by formula:

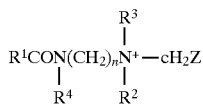

wherein $R^1$ is $C_8$–$C_{22}$ alkyl or alkenyl, preferably $C_{12}$–$C_{16}$, $R^2$ is hydrogen or $CH_2CO_2M$, $R^3$ is $CH_2CH_2OH$ or $CH_2CH_2OCH_2CH_2COOM$, $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal, alkaline earth metal, or ammonium. Examples of "alkali metal" include lithium, sodium, and potassium. Examples of "alkaline earth metal" include beryllium, magnesium, calcium, strontium, and barium. This type of surfactant is sometimes classified as an imidazoline-type amphoteric surfactant, although it should be recognized that it does not necessarily have to be derived, directly or indirectly, through an imidazoline intermediate.

Suitable materials of this type are marketed under the tradename MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Specific commercial products providing the amphoteric surfactant component of the present compositions include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine surfactant suitable for use herein can be depicted by compounds having the formula:

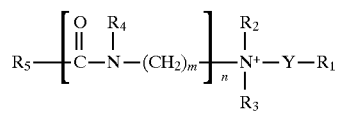

Wherein:

$R_1$ is a member selected from the group consisting of

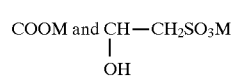

$R_2$ is lower alkyl or hydroxyalkyl;

$R_3$ is lower alkyl or hydroxyalkyl;

$R_4$ is a member selected from the group consisting of hydrogen and lower alkyl;

$R_5$ is higher alkyl or alkenyl;

Y is lower alkyl, preferably methyl;

m is an integer from 2 to 7, preferably from 2 to 3;

n is the integer 1 or 0;

M is hydrogen or a cation, as previously described, such as an alkali metal, alkaline earth metal, or ammonium.

The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substitutents such as hydroxyl or halogen radicals wherein the radical remains of hydrophobic character.

Examples of surfactant betaines of the above formula wherein n is zero which are useful herein include the alkylbetaines such as cocodimethylcarboxymethylbetaine, lauryidimethylcarboxymethyl-betaine, lauryl dimethyl-alpha-carboxyethylbetaine, cetyldimethyl-carboxymethylbetaine, lauryl-bis-(2-hydroxyethyl) carboxymethyl-betaine, stearyl-bis-(2-hydroxypropyl) carboxymethylbetaine, oleyl-dimethyl-gamma-carboxypropylbetaine, lauryl-bix-(2-hydroxypropyl)-alpha-carboxyethylbetaine, etc. The sulfobetaines may be represented by cocodimethylsulfopropylbetaine, stearyldimethylsulfo-propylbetaine, lauryl-bis-(2-hydroxyethyl)sulfopropylbetaine, and the like.

Surfactant amido betaines and amidosulfo betaines useful in the present invention are exemplified by compounds of the above formula wherein n is one (1) but otherwise corresponding to the above examples. Examples include the amidocarboxybetaines, such as cocoamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocoamido-bis-(2-hydroxyethyl)-carboxymethylbetaine, etc. The amido sulfobetaines may be represented by cocoamidodimethylsulfopropylbetaine, stearylamidodimethylsulfopropylbetaine, lauryl-amido-bis-(2-hydroxyethyl)-sulfopropylbetaine, and the like.

Examples of amphoteric surfactants also include N-higher alkyl aspartic acids such as those produced according to the teaching of U.S. Pat. No. 2,438,091.

When used, amphoteric surfactants are typically present at levels of from about 0.5% to about 20%, more typically from about 1 % to about 10%, although higher or lower levels can be used.

Nonionic Surfactants

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are:

1. The polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol.

2. Those derived from the condensation of ethylene oxide with the product resulting from the reaction of propylene oxide and ethylene diamine products.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$R_1R_2R_3N \rightarrow O$ wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond.

5. Long chain tertiary phosphine oxides corresponding to the following general formula:

$RR'R''P \rightarrow O$ wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.

7. Alkyl polysaccharide (APS) surfactants such as the alkyl polyglycosides. Such surfactants are described in U.S. Pat. No. 4,565,647, Llenado, issued Jan. 21, 1986, incorporated herein by reference, which discloses APS surfactants having a hydrophobic group with about 6 to about 30 carbon atoms and polysaccharide (e.g., polyglycoside) as the hydrophilic group. Optionally, there can be a polyalkylene-oxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).

8. Polyethylene glycol (PEG) glyceryl fatty esters, such as those of the formula $R(O)OCH^2CH(OH)CH^2(OCH^2CH^2)_nOH$ wherein n is from about 5 to about 200, preferably from about 20 to about 100, and R is an aliphatic hydrocarbyl having from about 8 to about 20 carbon atoms. When used, amphoteric surfactants are typically present at levels of from about 0.5% to about 20%, more typically from about 1% to about 10%, although higher or lower levels can be used.

Preferred shampoos of the present invention contain combinations of anionic surfactants with zwitterionic surfactants and/or amphoteric surfactants. Especially preferred shampoos contain from 0% to about 16% of alkyl sulfates, from 0% to about 16% of ethoxylated alkyl sulfates, and from 0% to about 10% of detersive surfactants selected from the nonionic, amphoteric, and zwitterionic detersive surfactants, with at least 5% of either alkyl sulfate, ethoxylated alkyl sulfate, or a mixture thereof, more perferably at least about 7%, and a total surfactant level of from about 10% to about 25%.

Hair Conditioning Agents

The compositions of the present invention also contain as an essential component one or more nonvolatile hair conditioning agents selected from the group consisting of insoluble silicones and water soluble, organic cationic conditioning agents such as cationic surfactants and cationic polymers. Preferably, a combination of the silicones and cationic surfactant and/or polymer is used.

Silicone Hair Conditioning Agent

The silicone hair conditioning agent component of the present invention is nonvolatile and insoluble in the composition. Typically it will be intermixed in the shampoo composition so as to be in the form of a separate, discontinuous phase of dispersed, insoluble particles, also referred to as droplets. These droplets are preferably suspended with a suspending agent, numerous, nonexclusive suitable examples of which are described below. The silicone hair conditioning agent phase will comprise a silicone fluid hair conditioning agent such as a silicone fluid and can also comprise other ingredients, such as a silicone resin to enhance silicone fluid deposition efficiency or enhance glossiness of the hair (especially when high refractive index (e.g. above about 1.46) silicone conditioning agents are used (e.g. highly phenylated silicones).

The term "nonvolatile" as used herein shall mean that the silicone material exhibits very low or no significant vapor pressure at ambient conditions, as is understood by those in the art. Boiling point at one atmosphere will preferably be at least about 250° C., more preferably at least about 275° C., most preferably at least about 300° C. Vapor pressure is preferably about 0.2 mm HG at 25° C. or less, preferably about 0.1 mm HG at 25° C. or less.

The silicone hair conditioning agent phase may comprise volatile silicone components. Typically, if volatile silicones are present, it will be incidental to their use as a solvent or carrier for commercially available forms of nonvolatile silicone materials ingredients, such as silicone gums and resins.

The silicone hair conditioning agent component for use herein will preferably have viscosity of from about 20 to about 2,000,000 centistokes at 25° C., more preferably from about 1,000 to about 1,800,000, even more preferably from about 50,000 to about 1,500,000, most preferably from about 100,000 to about 1,500,000. The viscosity can be measured by means of a glass capillary viscometer as set forth in Dow Corning Corporate Test Method CTM0004, Jul. 20, 1970.

The silicone hair conditioning agent component will generally be used in the shampoo compositions hereof at levels of from about 0.05% to about 10% by weight of the composition, preferably from about 0.1% to about 10%, more preferably from about 0.5% to about 8%, most preferably from about 0.5% to about 5%. The minimum level that is used in a particular composition should be effective to provide a conditioning benefit. The maximum level that can be used is not limited by theory, but rather by practicality. It is generally unnessary and expensive to use levels in excess of about 10%, although higher levels can be used if desired.

One type of silicone fluid that can be used herein is a silicone oil. The term "silicone oil" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000. Suitable silicone oils include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used.

More particularly silicone oils hereof include polyalkyl or polyaryl siloxanes with the following structure (I):

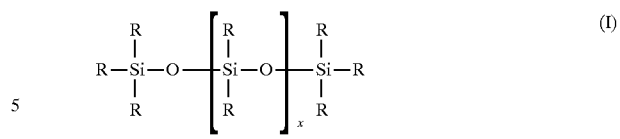

wherein R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, are insoluble in the composition, and are capable of being deposited on and, of conditioning, the hair.

The two R groups on the silicon atom of each monomeric silicone unit may represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl -3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Alkylamino substituted silicones that can be used herein include those of the formula II:

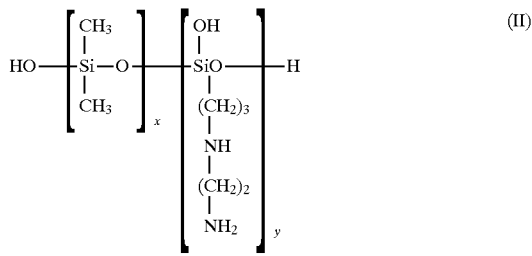
(II)

in which x and y are integers which depend on the molecular weight, the average molecular weight being approximately between 5,000 and 10,000. This polymer is also known as "amodimethicone".

Cationic silicone fluids which can be used in the present compositions include those that correspond to the formula III:

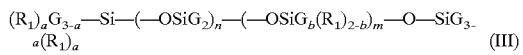
(III)

in which G is chosen from the group consisting of hydrogen, phenyl, OH, $C_1$–$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups

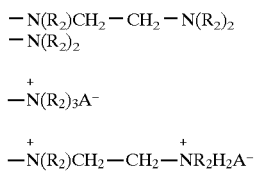

in which $R_2$ is chosen from the group consisting of hydrogen, phenyl, benzyl, a saturated hydrocarbon radical, preferably an alkyl radicalcontaining from 1 to 20 carbon atoms, and $A^-$ denotes a halide ion.

An especially preferred cationic silicone corresponding to formula (III) is the polymer known as "trimethylsilylamodimethicone", of formula (IV):

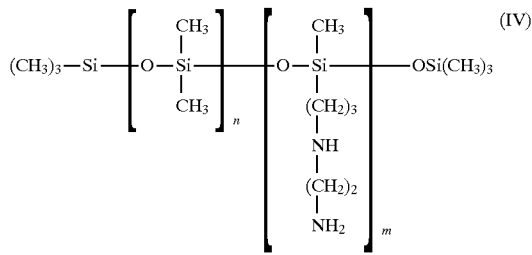
(IV)

Other silicone cationic polymers which can be used in the present compositions correspond to the formula V:

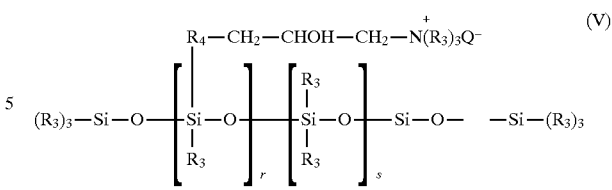
(V)

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$–$C_{18}$ alkylene radical or a $C_1$–$C_{18}$, and preferably $C_1$–$C_8$, alkyleneoxy radical;

$Q^-$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Another silicone fluid that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane oil having a viscosity of from about 10 centistokes to about 100,000 centistokes, wherein the ratio of gum to fluid is from about 30:70 to about 70:30, preferably from about 40:60 to about 60:40.

Another category of nonvolatile, insoluble silicone fluid conditioning agents are high refractive index silicones, having a refractive index of at least about 1.46, preferably at least about 1.48, more preferably at least about 1.52, most preferably at least about 1.55. Although not intended to necessarily be limiting, the refractive index of the polysiloxane fluid will generally be less than about 1.70, typically less than about 1.60. Polysiloxane "fluid" includes oils as well as gums.

The high refractive index polysiloxane fluid suitable for purposes hereof includes those represented by general Formula (I) above, as well as cyclic polysiloxanes such as those represented by Formula (VI),below:

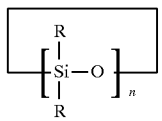 (VI)

wherein R is as defined above, n is from about 3 to about 7, preferably from 3 to 5.

The high refractive index polysiloxane fluids hereof contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids hereof will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids hereof are also characterized by relatively high surface tensions as a result of their aryl substitution. In general, the polysiloxane fluids hereof will have a surface tension of at least about 24 dynes/cm$^2$, typically at least about 27 dynes/cm$^2$. Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

The preferred high refractive index polysiloxane fluids hereof will have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially $R^1NHR^2NH^2$ where each $R^1$ and $R^2$ independently is a $C_1$–$C_3$ alkyl, alkenyl, and/or alkoxy.

High refractive index polysiloxane are available commercially from Dow Corning Corporation (Midland, Mich., U.S.A.) Huls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

Also, the spreading agent will preferably reduce the surface tension by at least about 2 dynes/cm$^2$, preferably at least about 3dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably 30 dynes/cm$^2$ or less, more preferably about 28 dynes/cm$^2$ or less most preferably about 25 dynes/cm$^2$ or less. Typically the surface tension will be in the range of from about 15 to about 30, more typically from about 18 to about 28, and most generally from about 20 to about 25 dynes/cm$^2$.

The weight ratio of the highly arylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios may be effective due to the efficiency of these surfactants. Thus is contemplated that ratios significantly above 1000:1 may be used.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporatedherein by reference is Silicon Compounds distributed by Petrarch Systems, Inc., 1984. This reference provides an extensive (though not exclusive) listing of suitable silicone fluids.

An optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of conditioning agent in the composition.

Cationic Hair Conditioning Agent

The compositions of the present invention can also comprise a water soluble, cationic hair conditioning agent. The cationic hair conditioning agent hereof will generally be present at levels of from about 0.05% to about 5%, preferably from about 0.1% to about 4%, more preferably from about 0.2% to about 3%, by weight, of the shampoo composition. The water soluble cationic conditioning agents hereof can include organic cationic polymers, organic cationic surfactants, and cationic silicone fluids.

By "water soluble", what is meant is a material which is soluble in water at a concentration of 0.1 % in water (distilled or equivalent) at 25° C. Preferably, the water soluble cationic conditioning agent will be soluble at 0.5% concentration, more preferably at 1.0% concentration. In general, the polymer will be considered soluble if it forms a substantially clear solution to the naked eye Water Soluble Cationic Polymers The cationic polymers useful in the hair conditioning agent hereof are polymers that can provide conditioning benefits to hair and that are soluble in the shampoo composition. Any cationic polymers which can provide these benefits can be used. As used herein, the term "polymer" shall include materials whether made by polymerization of one type of monomer or made by two (i.e., copolymers) or more types of monomers.

The cationic organic polymers hereof will generally have a weight average molecular weight which is at least about 5,000, typically at least about 10,000, and is less than about 10 million. Preferably, the molecular weight is from about 100,000 to about 2 million. The cationic polymers will have cationic nitrogen-containing moieties such as quaternary ammonium or cationic amino moieties, or a mixture thereof.

Those skilled in the art will recognize that the charge density of amino-containing polymers may vary depending upon pH and the isoelectric point of the amino groups. The polymer should be within the above solubility limits at the pH of intended use, which will in general be from about pH 3 to about pH 9, most generally from about pH 4 to about pH 8.

Any anionic counterions can be utilized for the cationic polymers so long as the water solubility criteria is met. Suitable counterions include halides (e.g., Cl, Br, I, or F, preferably Cl, Br, or I ), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are $C_1$–$C_7$ alkyls, preferably lower alkyls such as the $C_1$–$C_3$ alkyls, more preferably $C_1$ and $C_2$ alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyidiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

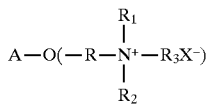

wherein: A is an anhydroglucose residual group, such as a starch or cellulose anhydroglucose residual, R is an alkylene oxyalkylene, polyoxyalkylene, or hydroxyalkylene group, or combination thereof, R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

As discussed above, the cationic polymer hereof is water soluble. This does not mean, however, that it must be soluble in the shampoo composition. Preferably however, the cationic polymer is either soluble in the shampoo composition, or in a coacervate phase in the shampoo composition formed by the cationic polymer and anionic material. Coacervates of the cationic polymer can be formed with anionic surfactants or with anionic polymers that can optionally be added to the compositions hereof (e.g., sodium polystyrene sulfonate).

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters has previously been studied. See, for example, J. Caelles, et al., "Anionic and Cationic Compounds in Mixed Systems", Cosmetics & Toiletries, Vol. 106, Apr. 1991, pp 49–54, C. J. van Oss, "Coacervation, Complex-Coacervation and Flocculation", J. Dispersion Science and Technology, Vol. 9 (5,6), 1988–89, pp 561–573, and D. J. Burgess, "Practical Analysis of Complex Coacervate Systems", J. of Colloid and Interface Science, Vol. 140, No. 1, November 1990, pp 227–238.

It is believed to be particularly advantageous for the cationic polymer to be present in the shampoo in a coacervate phase, or to form a coacervate phase upon application or rinsing of the shampoo to or from the hair. Coacervates are believed to more readily deposit on the hair. Thus, in general, it is preferred that the cationic polymer exist in the shampoo as a coacervate phase or form a coacervate phase upon dilution. If not already a coacervate in the shampoo, the cationic polymer will preferably exist in a coacervate form in the shampoo upon dilution with water to a water-:shampoo composition weight ratio of about 20:1, more preferably at about 10:1, even more preferably at about 8:1.

Techniques for analysis of formation of coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

Exemplary coacervate shampoo compositions are shown in the examples. Many other cationic polymers, depending upon the other parameters of the shampoo composition, can also form coacervates, as will be understood by those skilled in the art.

Water Soluble Cationic Surfactants

The compositions of the present invention can comprise one or more organic, water soluble, cationic surfactants useful for the conditioning of hair, hereinafter "cationic surfactant", selected from the group consisting of quaternary ammonium surfactants and amino surfactants that are positively charged at the pH of the shampoo composition. The shampoo compositions will generally contain from about 0.2% to about 10%, preferably from about 0.5% to about 8%, more preferably from about 1 % to about 5%, of the water soluble cationic conditioning agent. The cationic surfactants for use herein also must contain one or more nonionic hydrophilic moieties. Sufficient hydrophilic moieties must be present to maintain solubility subsequent to any ionic complexation that may occur between the cationic conditioning surfactants and the anionic detersive surfactants.

The preferred cationic surfactants for use in the present invention are those which are useful for providing conditioning benefits, particularly hair conditioning properties and which are quaternary ammonium or amino compounds having at least one N-radical containing one or more nonionic hydrophilic moieties selected from alkoxy, polyoxyalkylene, alkylamido, hydroxyalkyl, and alkylester moieties, and combinations thereof.

In preferred embodiments, the surfactant contains at least one hydrophilic moiety within 4 (inclusive), preferably within 3 (inclusive), carbon atoms of the quaternary nitrogen or cationic amino nitrogen. For purposes herein, this means that the closest non-carbon atom in the hydrophilic moiety to the cationic nitrogen must be within the stated number of carbon atoms relative to said nitrogen. Additionally, carbon atoms that are part of a hydrophilic moiety, e.g., carbon atoms in a hydrophilic polyoxyalkylene (e.g., —$CH_2$—$CH_2$—O—), that are adjacent to other hydrophilic moieties are not counted as when determining the number of hydrophilic moieties within 4, or preferably 3, carbon atoms of the cationic nitrogen. In general, the alkyl portion of any hydrophilic moiety is preferably a $C_1$–$C_3$ alkyl. Suitable hydrophile-containing radicals include, for example, ethoxy, propoxy, polyoxyethylene, polyoxypropylene, ethylamido, propylamido, hydroxymethyl, hydroxyethyl, hydroxypropyl, methylester, ethylester, propylester, or mixtures thereof, as nonionic hydrophile moieties. The amino surfactants must be positively charged at the pH of the shampoo compositions. Generally, the pH of the shampoo compositions will be less than about 10, typically from about 3 to about 9, preferably from about 4 to about 8.

Among the quaternary ammonium cationic surfactants useful herein are those of the general formula:

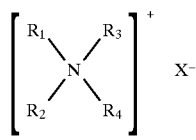

wherein $R_1$, $R_2$, $R_3$ and $R_4$ radicals comprise, independently, substituted or unsubstituted hydrocarbyl chains of from 1 to about 30 carbon atoms, or a hydrocarbyl having from 1 to about 30 carbon atoms and containing one or more aromatic, ether, ester, amido, or amino moieties present as substituents or as linkages in the radical chain, wherein at least one of the $R_1$–$R_4$ radicals contains one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Preferably, the cationic conditioning surfactant contains from 2 to about 10 nonionic hydrophile moieties located within the above stated ranges. For purposes herein, each hydrophilic amido, alkoxy, hydroxyalkyl, alkylester, alkylamido or other unit is considered to be a distinct nonionic hydrophile moiety. X is a soluble salt forming anion preferably selected from halogen (especially chlorine), acetate, phosphate, nitrate, sulfonate, and alkyl sulfate radicals.

Preferred quaternary ammonium salt surfactants include those of the formula

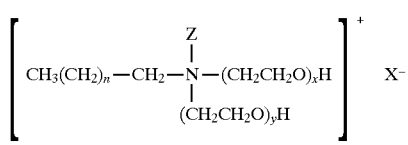

wherein n is from 8–28, preferably 16, x+y =2 to about 15. Z is a short chain alkyl, preferably a $C_1$–$C_3$ alkyl, more preferably methyl, and X is a water soluble salt forming anion (e.g., Cl, sulfate, methosulfate, etc.)

Other preferred quaternary ammonium salt surfactants include those of the formula

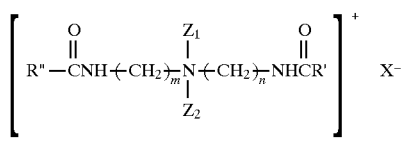

wherein $Z_1$ and $Z_2$ are, independently, substituted or unsubstituted hydrocarbyls, and, preferably, $Z_1$ is an alkyl, preferably a $C_1$–$C_3$ alkyl, more preferably methyl, and $Z_2$ is a short chain hydroxyalkyl, preferably hydroxymethyl or hydroxyethyl, n and m independently are integers from 2 to 4, inclusive, preferably from 2 to 3, inclusive, more preferably 2, R' and R", independently, are substituted or unsubstituted hydrocarbyls, preferably $C_{12}$–$C_{20}$ alkyl or alkenyl, and X is a soluble salt-forming anion (e.g., sulfate, methosulfate, Cl, etc.).

Still other quaternary ammonium salt surfactants are of the formulas:

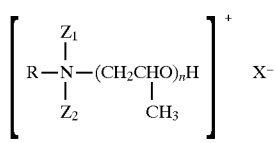

wherein R is a hydrocarbyl, preferably a $C_1$–$C_3$ alkyl, more preferably methyl, $Z_1$ and $Z_2$ are, independently, short chain hydrocarbyls, preferably $C_2$–$C_4$ alkyl or alkenyl, more preferably ethyl, n is from about 2 to about 40, preferably from about 7 to about 30, and X is a soluble-salt forming anion, as set forth previously;

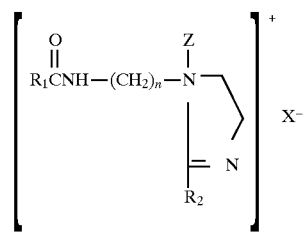

wherein $R_1$ and $R_2$, independently, are $C_{12}$–$C_{20}$ hydrocarbyls, preferably $C_{16}$–$C_{18}$ alkyl or alkenyls (e.g., those derived from tallow acid), Z is a $C_1$–$C_3$ hydrocarbyl, preferably methyl, n is 2 or 3, and X is a soluble salt forming anion; and

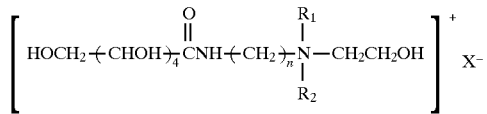

wherein n is 2 or 3, $R_1$ and $R_2$, independently are $C_1$–$C_3$ hydrocarbyls preferably methyl, and X is as defined above.

Specific examples of preferred quaternary ammonium salts include polyoxyethylene (2) stearyl methyl ammonium chloride, methyl bis (hydrogenated tallowamidoethyl) 2-hydroxyethyl ammonium methyl sulfate, polyoxypropylene (9) diethyl methyl ammonium chloride, tripolyoxyethylene (total PEG=10) stearyl ammonium phosphate, bis(N-hydroxyethyl-2-oleyl imidazolinium chloride) polyethylene glycol (12), and isododecylbenzyl triethanolammonium chloride.

Other quaternary ammonium and amino surfactants include those of the above general formula I in the form of ring structures formed by covalently linking of the radicals. Examples of such cationic surfactants include imidazolines, imidazoliniums, and pyridiniums, etc., wherein said surfactant has at least one nonionic hydrophile-containing radical as set forth above. Specific examples include 2-heptadecyl4,5-dihydro-1H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxooctadecyl)oxy]ethyl]amino]ethyl] pyridinium chloride.

Salts of primary, secondary and tertiary fatty amines are also preferred cationic surfactant materials. The alkyl groups of such amines preferably have from about 1 to about 30 carbon atoms and must contain at least one, preferably 2 to about 10, nonionic hydrophilic moieties selected from alkoxy, polyoxyalkylene, alkylamido, hydroxyalkyl, and alkylester moieties, and mixtures thereof. Secondary and tertiary amines are preferred, tertiary amines are particularly preferred. Specific examples of suitable amines include diethyl aminoethyl polyoxyethylene (5) laurate, coco-polyglyceryl-4 hydroxypropyl dihydroxy ethylamine, and dihydroxyethyl tallowamine hydrochloride.

The cationic conditioning agents for use herein may also include a plurality of ammonium quaternary moieties or amino moieties, or a mixture thereof.

Polyvalent Metal Cation

Another essential component in the compositions of the present invention is a polyvalent metal cation, or mixture of polyvalent cations, suitable for topical use in cosmetic products in free ion form. Thus, the polyvalent metal cation can be added as a soluble metal salt or metal hydroxide. The salt can be in the form of a surfactant, such as an anionic surfactant (including the anionic detersive surfactants described above), or an inorganic salt, such as an acetate, halide (e.g. chloride), nitrate, or sulfate. Preferred inorganic salts are chloride, sulfate, and acetate.

Suitable polyvalent metal cations include divalent and trivalent metals, with divalent metals being preferred. Exemplary metal cations include alkaline earth metals, such as magnesium, and calcium, zinc and copper and trivalent metals, such as aluminum and iron. Most preferred are calcium and magnesium.

The polyvalent metal cation component should be present in the composition in soluble, free ion form.

The concentration of polyvalent metal cations in the composition in soluble free ion form should be from about 0.004M to about 0.08M, preferably from about 0.008M to about 0.04M, most preferably from about 0.01M to about 0.02M.

It will be clear to those skilled in the art that, based upon the amount of anionic surfactant that is preferably present (at least about 5%, by weight, of the composition), if polyvalent salts of the anionic surfactant is used as the mode of introducing the polyvalent metal cations into the compositions hereof, only a fraction of the anionic surfactant should generally be of polyvalent form, the remainder of the anionic surfactant being necessarily added in monovalent form. As lower levels of polyvalent cation are used, significant effects on conditioning agent are more difficult to obtain. As the level increases above the upper limit, the additional polyvalent metal cation becomes unnecessary for practical reasons, providing little additional benefit in conditioning performance, reduced foaming, and tends to cause decreased viscosity which is disadvantageous aesthetically and adversely affects effective suspension of insoluble, discontinuous phases (e.g. silicone, particulate anti-dandruff agents, particulate anti-static cationic surfactants, etc.) that may be present in the composition.

Hardness of the shampoo compositions can be measured by standard methods in the art, such as by ethylene diamine tetraacetic acid (EDTA) titration. In the event that the composition contains dyes or other color materials that interfere with the ability of EDTA titration to yield a perceptible color change, hardness should be determined for the composition in the absence of the interfering dye or color.

Water

The compositions of the present invention will comprise form about 20% to about 99.5%, preferably from about 50% to about 94.95%, more preferably from about 60% to about 85%, by weight, of water. It is preferred to use deionzed water when making the compositions hereof. Polyvalent metal cations are added to the compositions in salt or base form to increase the free polyvalent cation level in the final composition to within the prescribed range.

Alternately, tap water or other non-deionzed water can be used, and the free polyvalent metal cation level can be adjusted accordingly taking into consideration the amount of free cations in the water. Free polyvalent metal cation level can be increased, as applicable, to within the prescribed ranges as previously discribed. Alternately, if applicable, the level of free polyvalent metal cations can be decreased by partially deionzing the water or by adding a sequestery agent or a chelating agent to the composition (e.g., ethylene diamine tetraacetic acid).

Shampoo Compositions

The shampoo compositions of the present invention are intended for application to the hair and scalp, and will typically be applied using the hands and fingers. The compositions hereof must therefore be safe and suitable for frequent (e.g. daily) use. Ingredients which would not be suitable for frequent application to the hair or scalp, should not be used at levels which would not be acceptable for frequent use, or which could cause undue irritation or damage to the hair or skin. The present hair care compositions are essentially free of such materials. Exemplary materials which should not be included, or if included can be present only at very low levels include enzymes.

Additionally, the present compositions preferably will not contain large amounts of ingredients that tend to complex with the soluble polyvalent metal cations. Materials which would tend to do this include builders and sequestering agents, which complex with free polyvalent metal cations and tend to reduce the effects of hardness in water, and . In general, it is preferred that the composition contain about 0.1% or less of such materials. When they are present, the level of polyvalent metal cations in free ionic form can be adjusted to compensate for builders and sequestering agents by increasing the amount of polyvalent metal cations added to, or retained in, the composition.

Optional Ingredients

A variety of optional ingredients are described below. the description below is exemplary in nature and it is not intended to exclude other ingredients which are not inconsistent with the purposes of the present invention.

Suspending Agent

Any suspending agent useful for suspending the silicone hair conditioning agent in dispersed form in the shampoo compositions hereof is preferably used. A suspending agent is particularly important in pourable liquid formulations.

The preferred suspending agents in the present compositions are long chain acyl derivative materials, long chain amine oxides, or mixtures of such materials wherein such suspending agents are present in the composition in crystalline form. These suspending agents are described in U.S. Pat. No. 4,741,855, Grote and Russell, issued May 3, 1988, incorporated herein by reference. Included are ethylene glycol esters of fatty acids preferably having from about 16 to about 22 carbon atoms. More preferred are the ethylene glycol stearates, both mono and distearate, but particularly the distearate containing less than about 7% of the mono stearate. Other suspending agents found useful are alkanol amides of fatty acids, preferably having from about 16 to about 22 carbon atoms, more preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Suspending agents also include long chain amine oxides such as alkyl ($C_{16}$–$C_{22}$) dimethyl amine oxides, e.g., stearyl dimethyl amine oxide. If the compositions contain an amine oxide or a long chain acyl derivative which is a surfactant, the suspending function could also be provided by such amine oxide or surfactant and additional suspending agent may not be needed.

Other long chain acyl derivatives that can be used include N,N-dihydrocarbyl amido benzoic acid and soluble salts thereof (e.g., Na and K salts), particularly N,N-di (hydrogenated) $C_{16}$, $C_{18}$ and tallow amido benzoic acid species of this family, which are commercially available from Stepan Company (Northfield, Ill., USA).

The acyl derivative and amine oxide suspending agents are typically present in pourable, liquid formulations at a level of from about 0.1% to about 5.0%, preferably from about 0.5% to about 3.0%. The suspending agent serves to assist in suspending the silicone material and may give pearlescence to the product. Mixtures of suspending agents are also suitable for use in the compositions of this invention.

Another type of suspending agent that can be used is xanthan gum. Shampoo compositions utilizing xanthan gum as a suspending agent for the silicone hair conditioning component are described in U.S. Pat. No. 4,788,006, Bolich and Williams, issued Nov. 29, 1988, incorporated herein by reference. Xanthan gum is biosynthetic gum material that is commercially available. It is a heteropolysaccharide with a molecular weight of greater than 1 million. It is believed to contain D-glucose, D-mannose and D-glucuronate in the molar ratio of 2.8:2.0:2.0. the polysaccharide is partially acetylated with 4.7% acetyl. This information and other is found in Whistler, Roy L. Editor *Industrial Gums—Polysaccharides and Their Derivatives* New York: Academic Press, 1973. Kelco, a Division of Merck & Co., Inc. offers xanthan gum as KeltroIR. The gum, when used as the silicone hair conditioning component suspending agent, will typically be present in pourable, liquid formulations at a level of from about 0.3% to about 3%, preferably from about 0.4% to about 1.2% in the compositions of the present invention.

Combinations of long chain acyl derivatives and xanthan gum are disclosed as a suspending agent for silicone hair conditioners in U.S. Pat. No. 4,704,272, Oh et al., issued Nov. 3, 1987, incorporated herein by reference, and may also be used in the present compositions.

Another type of suspending agent that can be used is carboxyvinyl polymer. Preferred polymers are copolymers of acrylic acid crosslinked with polyallylsucrose as described in U.S. Pat. No. 2,798,053, Brown, issued Jul. 2, 1957, incorporated herein by reference. These polymers are provided by B. F. Goodrich Company as, for example, Carbopol 934, 940, 941, and 956.

A carboxyvinyl polymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to product carboxyvinyl polymers include polyols selected from the class consisting of oligosaccharides, reduced derivatives thereof in which the carbonyl group is converted to an alcohol group, and pentaerythritol;. more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids of the structure

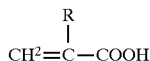

where R is a substituent selected from the group consisting of hydrogen and lower alkyl groups; most preferred is acrylic acid.

Preferred carboxyvinyl polymers used in formulations of the present invention have a molecular weight of at least about 750,000; more preferred are carboxyvinyl polymers having a molecular weight of at least about 1,250,000; most preferred are carboxyvinyl polymers having a molecular weight of at least about 3,000,000.

Other materials can also be used as suspension agents, including those that can impart a gel-like viscosity to the composition, such as water soluble or colloidally water soluble polymers like cellulose ethers (e.g., hydroxyethyl cellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

The suspending agents, in general, are used at a level of from about 0.1% to about 10%, most commonly from about 0.3% to about 5.0% by weight of the composition.

Hair Conditioning Oil

The shampoo compositions of the present invention can also comprise a nonvolatile, water insoluble, organic, oil liquid as a preferred, optional hair conditioning agent. The hair conditioning oily liquid can add shine and luster to the hair. Additionally, it can also enhance dry combing and dry hair feel. The hair conditioning oil liquid is typically present in the compositions at a level of from about 0.05% to about 5%, by weight of the composition, preferably from about 0.2% to about 3%, more preferably from about 0.5% to about 1%.

By "nonvolatile" what is meant is that the oily material exhibits very low or no significant vapor pressure at ambient conditions (e.g., 25° C.), as is understood in the art, in general, less than 0.2 mm Hg at 25° C. The nonvolatile oil preferably has a boiling point at ambient pressure of about 250° C. or higher.

By "water insoluble" what is meant is that the oily liquid is not soluble in water (distilled or equivalent) at a concentration of 0.1%, at 25° C.

The hair conditioning oily liquids hereof generally will have a viscosity of about 3 million cs or less, preferably about 2 million cs or less, more preferably about 1.5 million cs or less.

The hair conditioning oily materials hereof are liquids selected from the group consisting of hydrocarbon oils and fatty esters. The fatty esters hereof are characterized by having at least 10 carbon atoms, and include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 19 carbon atoms, although it is not necessarily meant to be limit the hydrocarbons to this range. Branched chain hydrocarbon oils can and typically may contain higher numbers of carbon atoms. Also encompassed herein are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 500, preferably from about 200 to about 400, more preferably from about 300 to about 350. Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, aswell as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A preferred hydrocarbon polymer is polybutene, such as the copolymer of isobutylene and butene. A commercially available material of this type is L-14 polybutene from Amoco Chemical Co. (Chicago, Ill., U.S.A.).

Monocarboxylic acid esters hereof include esters of alcohols and/or acids of the formula R'COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. The monocarboxylic acid ester however need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and tri-alkyl and alkenyl esters of carboxylic acids can also be used. These include, for example, esters of $C^4$–$C^8$ dicarboxylic acids such as $C^1$–$C^{22}$ esters (preferably $C^1$–$C^6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearyol stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain carboxylic acids, such as $C^1$–$C^{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils. include triolein and tristearin glyceryl dilaurate. Preferred glycerides are di-, and tri-glycerides. Especially preferred are triglycerides.

Other Optional Components

The compositions herein can contain a variety of non-essential optional components. Such optional ingredients include, for example, preservatives such as benzyl alcohol, methyl paraben, propyl paraben and imidazolidinyl urea; fatty alcohols; block polymers of ethylene oxide and propylene oxide such as Pluronic F88 offered by BASF Wyandotte; sodium chloride, sodium sulfate; ammonium xylene sulfonate; propylene glycol; polyvinyl alcohol; ethyl alcohol; pH adjusting agents such as citric acid, succinic acid, phosphoric acid, sodium hydroxide, sodium carbonate, etc.; perfumes; and dyes. These optional ingredients are typically used at levels of from about 0.01% to about 10% of the composition. This list of optional ingredients is not meant to be exclusive, and other optional components can be utilized.

Another optional ingredient that can be advantageously used is an anti-static agent, such as a water-insoluble cationic surfactant. The anti-static agent should not unduly interfere with the in-use performance and end-benefits of the shampoo; particularly, the anti-static agent should not interfere with the anionic detersive surfactant. Suitable anti-static agents include, for example, tricetyl methyl ammonium chloride. Typically, from about 0.1% to about 5% of such anti-static agent is incorporated into the shampoo compositions.

Still other optional materials include particulate antidandruff agents such as pyridinethione salts, especially those in platelet form, as disclosed in U.S. Pat. Nos. 4,379,753 and 4,345,080, incorporated herein by reference. Included, for example, are heavy metal (e.g., zinc), magnesium, and aluminum salts of 1-hydroxy-2-pyridimethione. Other antidandruff agents include selenium compounds such as selenium disulfide. Insofar as these materials are generally insoluble, they do not contribute to the level of polyvalent metal cations in free ionic form. Soluble antidandruff agents can also be used. Antidandruff agents are normally used at levels of about 0.1% to about 4% of the composition, preferably about 0.2% to about 2%.

Pediculicides can also be included in the compositions hereof to provide control of lice infestations. Suitable pediculicides are well known in the art and include, for example, pyrethrins such as those disclosed in U.S. Pat. No. 4,668,666, Allan, incorporated herein by reference.

METHOD OF MANUFACTURE

The compositions of the present invention, in general, can be made by mixing together at elevated temperature, e.g., about 72° C. water and surfactants along with any solids that need to be melted, to speed mixing into the shampoo. Additional ingredients can be added either to this hot premix or after cooling the premix. The ingredients are mixed thoroughly at the elevated temperature and then pumped through a high shear mill and then through a heat exchanger to cool them to ambient temperature. The silicone may be emulsified at room temperature in concentrated surfactant and then added to the cooled product. Alternately, for example, the silicone conditioning agent can be mixed with anionic surfactant and fatty alcohol, such as cetyl and stearyl alcohols, at elevated temperature, to form a premix containing dispersed silicone. The premix can then be added to and mixed with the remaining materials of the shampoo, pumped through a high shear mill, and cooled. The average particle size of the silicone is preferably from about 0.5 to about 20 microns.

METHOD OF USE

The present compositions are used in a conventional manner for cleaning and conditioning hair on human heads with a single product. An effective amount of the composition for cleaning and conditioning hair, typically, from about 1 g to about 20 g of the composition, is applied to hair that has preferably been wetted, generally with water, and then rinsed out. Application to the hair typically includes working the composition through the hair, generally with the hands and fingers, such that most or all of the hair is contacted with the composition.

EXAMPLES

The following examples illustrate the present invention. It will be appreciated that other modifications of the present invention within the skill of those in the hair care formulation art can be undertaken without departing from the spirit and scope of this invention.

All parts, percentages, and ratios herein are by weight unless otherwise specified. Some components may come from suppliers as dilute solutions. The levels given reflect the weight percent of the active material, unless otherwise specified. The excluded diluents and other materials are included in as "Minors". The "water" ingredient in the examples is deionzed water.

Example I

The following is an example of a shampoo composition of the present invention wherein the cationic polymer and anionic surfactant component form a coacervate phase.

| Component | Weight % |
| --- | --- |
| Ammonium Lauryl Sulfate | 13.5 |
| Ammonium Laureth (3) Sulfate | 4.0 |
| JAGUAR C-17[1] | 0.5 |
| Coconut Monoethanol Amide | 1.0 |
| Ethylene Glycol Distearate | 2.0 |
| Isocetyl Stearoyl Stearate | 1.0 |
| Tricetyl Methyl Ammonium Chloride | 0.5 |
| Polydimethylsiloxane[2] | 2.0 |
| Cetyl Alcohol | 0.4 |
| Stearyl Alcohol | 0.2 |
| Perfume | 1.0 |
| Color Solution | 0.6 |
| $MgSO_4 \cdot 7H_2O$ | 1.0 |
| Preservative | 0.4 |
| Water and Minors | to 100% |

[1]Tradename for guar hydroxypropyltrimonium chloride, a cationic polymer available from Rhone-Poulenc (Cranbury, NJ, USA).
[2]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning. As an alternative, the JAGUAR C-17 can be replaced with LUVIQUAT FC 370 (see Example III, footnote 1).

Example II

The following is an example of a shampoo composition of the present invention.

| Component | Weight % |
| --- | --- |
| Ammonium Lauryl Sulfate | 4.2 |
| Ammonium Laureth (3) Sulfate | 13.2 |
| POLYMER LR 400[1] | 1.0 |
| Coconut Monoethanol Amide | 1.0 |
| Ethylene Glycol Distearate | 2.0 |
| Light Mineral Oil | 1.0 |
| Tricetyl Methyl Ammonium Chloride | 0.5 |
| Polydimethylsiloxane[2] | 1.5 |
| Cetyl Alcohol | 0.4 |
| Stearyl Alcohol | 0.2 |
| Perfume | 1.2 |
| Color Solution | 0.6 |
| $CaCl_2$ | 0.4 |
| Preservative | 0.4 |
| Water and Minors | to 100% |

[1]Cellulose, 2-[2-hydroxy-3-(trimethyl ammonio)propoxy] ethyl ether, chloride, a cationic polymer available from Amerchol Corp. (Edison, NJ, USA).
[2]A 40/60 weight ratio blend of polydimethylsiloxane gum (GE SE 76, available from General Electric Co., Silicone Products Div., Waterford, NY, USA). and polydimethylsiloxane fluid (about 350 centistokes).

The composition can provide excellent in-use hair cleaning and conditioning

Example III

The following is a shampoo composition of the present invention.

| Component | Weight % |
| --- | --- |
| Ammonium Lauryl Sulfate | 13.5 |
| Ammonium Laureth (3) Sulfate | 4.0 |
| LUVIQUAT FC 370[1] | 0.5 |
| VARONIC LI-67[4] | 2.0 |
| Coconut Monoethanol Amide | 1.0 |
| Ethylene Glycol Distearate | 2.0 |
| Varisoft 110[2] | 1.0 |
| Tricetyl Methyl Ammonium Chloride | 0.5 |
| Polydimethylsiloxane[3] | 3.0 |
| Cetyl Alcohol | 0.4 |
| Stearyl Alcohol | 0.2 |
| Perfume | 1.0 |
| Color Solution | 0.6 |
| $MgSO_4 \cdot 7H_2O$ | 0.5 |
| Preservative | 0.4 |
| Water and Minors | 71.8 |

[1]Tradename of BASF Wyandotte Corporation (Parsippany, NJ, USA) for copolymer of vinyl pyrrolidone and methyl vinyl imidazolium chloride.
[2]Varisoft 110, methyl bis-hydrogenated tallow amido ethyl 2-hydroxyethyl ammonium methyl sulfate, available from Sherex Chemical Co.. Inc. (Dublin, Ohio, USA).
[3]A 40/60 weight ratio blend of polydimethylsiloxane gum (GE SE 76, available from General Electric Co., Silicone Products Div., Waterford, NY, USA) and polydimethylsiloxane fluid (about 350 centistokes).
[4]VARONIC LI-67 is a tradename for PEG-80 glyceryl cocoate, available from Sherex Chemical Co., Inc. (Dublin, Ohio, U.S.A.).

The composition can provide excellent in-use hair cleaning and conditioning. As an alternative, the LUVIQUAT FC 370 can be replaced with JAGUAR C-17 (see Example I, footnote 1).

Example IV

The following is an example of a shampoo composition of the present invention.

| Component | Weight % |
| --- | --- |
| Cocoamidopropyl Betaine | 4.0 |
| Ammonium Laureth (3) Sulfate | 12.0 |
| Coconut Monoethanol Amide | 2.0 |
| Luviquat FC 370 | 1.0 |
| Cetyl Hydroxyethylcellulose | 0.3 |
| Tricetyl Methyl Ammonium Chloride | 0.5 |
| Cetyl Alcohol | 0.4 |
| Stearyl Alcohol | 0.2 |
| Perfume | 1.0 |
| Color Solution | 0.6 |
| $AlCl_3$ | 0.2 |
| Preservative | 0.4 |
| Water and Minors | to 100% |

Example V

The following is a shampoo composition of the present invention.

| Component | Weight % |
| --- | --- |
| Ammonium Lauryl Sulfate | 4.6 |
| Ammonium Laureth (3) Sulfate | 15.4 |
| Coconut Monoethanol Amide | 1.0 |
| Ethylene Glycol Distearate | 2.0 |
| Tricetyl Methyl Ammonium Chloride | 0.5 |
| Polydimethylsiloxane[1] | 2.0 |
| Cetyl Alcohol | 0.4 |
| Stearyl Alcohol | 0.2 |
| Perfume | 1.0 |
| Color Solution | 0.6 |
| $Ca(C_2H_3O_2)_2$ | 0.5 |
| Preservative | 0.4 |
| Water and Minors | to 100% |

[1]A 40/60 weight ratio blend of polydimethylsiloxane gum (GE SE 76, available from General Electric Co., Silicone Products Div., Waterford, NY, USA) and polydimethylsiloxane fluid (about 350 centistokes).

EXAMPLE VI

The following is a shampoo composition of the present invention wherein the cationic polymer and anionic surfactant component form a

| Component | Weight % |
| --- | --- |
| Ammonium Lauryl Sulfate | 8.5 |
| Ammonium Laureth (3) Sulfate | 8.5 |
| Varisoft 110 | 1.0 |
| Coconut Monoethanol Amide | 1.0 |
| Ethylene Glycol Distearate | 2.0 |
| Tricetyl Methyl Ammonium Chloride | 0.5 |
| Polydimethylsiloxane[2] | 2.0 |
| Cetyl Alcohol | 0.4 |
| Stearyl Alcohol | 0.2 |
| Perfume | 1.0 |
| Color Solution | 0.6 |
| $ZnCl_2$ | 0.4 |
| Preservative | 0.4 |
| Water and Minors | to 100% |

[2]VISCASIL 600,000 cS, from General Electric, Waterford, NY, USA.

2 VISCASIL, 600,000 cS, from General Electric, Waterford, N.Y., USA.

The composition can provide excellent in-use hair cleaning and conditioning.

The example compositions hereof can be made by preparing a premix of the entire amount of silicone conditioning agent to be incorporated into the shampoo, along with sufficient ammonium laureth (3) sulfate and cetyl and stearyl alcohol such that the premix comprises about 30% silicone conditioning agent, about 69% surfactant, and about 1% of the alcohols. The premix ingredients are heated and stirred at 72° C. for about 10 minutes and the premix is then conventionally mixed with the remaining hot (72° C.) ingredients. The composition is then pumped through a high shear mixer and cooled.

What is claimed is:

1. A hair conditioning shampoo composition comprising:
   (a) from about 5% to about 50%, by weight, of a detersive surfactant, or mixture thereof, selected from the group consisting of anionic sulfate surfactants;
   (b) a nonvolatile hair conditioning agent selected from the group consisting of water soluble cationic conditioning agents, insoluble silicone conditioning agents and mixtures thereof; said cationic conditioning agents being present at a level of from about 0.05% to about 5%, by weight of the composition, and said insoluble silicone conditioning agents being present at a level of from about 0.05% to about 10%, by weight of the composition;
   (c) from about 20% to about 94.95%, by weight, of water;
   wherein said composition further comprises from about 0.004M to about 0.08M of magnesium cations in free ion form.

2. A hair conditioning shampoo composition as in claim 1, wherein said composition comprises an insoluble silicone conditioning agent and a water soluble cationic conditioning agent.

3. A hair conditioning shampoo composition as in claim 2, wherein said water soluble cationic conditioning agent is a cationic polymer.

4. A hair conditioning shampoo composition as in claim 2, wherein said water soluble cationic conditioning agent is a cationic surfactant.

5. A hair conditioning shampoo composition as in claim 1, comprising from about 0.008M to about 0.04M of said magnesium cations.

6. A hair conditioning shampoo composition as in claim 1, comprising from about 0.01M to about 0.02M, of said polyvalent metal cations.

7. A hair conditioning shampoo composition comprising:
   (a) from about 5% to about 50%, by weight, of an anionic sulfate detersive surfactant, or a mixture thereof;
   (b) from about 0.05% to about 10%, by weight, of an insoluble silicone hair conditioning component;
   (c) from about 20% to about 94.95%, by weight, of water;
   wherein said composition further comprises from about 0.004M to about 0.08M of magnesium cations in free ion form.

8. A hair conditioning shampoo composition as in claim 7, wherein said composition comprises from about 50% to about 94.9%, by weight, water, and further comprises from about 0.05% to about 5%, by weight, of a water soluble cationic conditioning agent, or mixture thereof.

9. A hair conditioning shampoo composition as in claim 8, wherein said water soluble cationic conditioning agent comprises a cationic polymer.

10. A hair conditioning shampoo composition as in claim 8, wherein said water soluble cationic conditioning agent comprises a cationic surfactant.

11. A hair conditioning shampoo composition comprising:
    (a) from about 5% to about 50%, by weight, of an anionic detersive surfactant, or mixture thereof,
    (b) from about 0.05% to about 5% by weight, of a water soluble cationic conditioning agent, or mixture thereof;
    (c) from about 10% to about 94.95%, by weight, of water;
    wherein said composition further comprises from about 0.004M to about 0.08M of magnesium cations in free ion form.

12. A hair conditioning shampoo composition as in claim 11, wherein said water soluble cationic conditioning agent comprises a cationic polymer.

13. A hair conditioning shampoo composition as in claim 11, wherein said water soluble cationic conditioning agent comprises a cationic surfactant.

14. A method for making a hair conditioning shampoo composition comprising combining:
    (a) from about 5% to about 50%, by weight, of a detersive surfactant, or mixture thereof, selected from the group consisting of anionic sulfate surfactants;
    (b) a nonvolatile hair conditioning agent selected from the group consisting of water soluble cationic conditioning agents and insoluble silicone conditioning agents; said cationic conditioning agents being present at a level of from about 0.05% to about 5%, by weight of the composition, and said insoluble silicone conditioning agents being present at a level of from about 0.05% to about 10%, by weight of the composition;
    (c) from about 20% to about 94.95%, by weight, of water;
    wherein said composition further comprises from about 0.004M to about 0.08M of magnesium cations in free ion form.

15. A method as in claim 14, wherein said magnesium cation level is adjusted to within the range of from about 0.008M to about 0.04M.

* * * * *